United States Patent [19]
Kato et al.

[11] Patent Number: 5,976,335
[45] Date of Patent: Nov. 2, 1999

[54] GAS SENSOR HAVING A FUNCTION FOR MINIMIZING HEATER LEAK CURRENT

[75] Inventors: Nobuhide Kato, Ama-gun; Yasuhiko Hamada, Nagoya, both of Japan

[73] Assignee: NGK Insulators, Ltd., Japan

[21] Appl. No.: 08/986,318

[22] Filed: Dec. 5, 1997

[30] Foreign Application Priority Data

Dec. 20, 1996 [JP] Japan .................................... 8-341250

[51] Int. Cl.[6] .................................................. G01N 27/26
[52] U.S. Cl. .......................... 204/425; 204/408; 204/426; 204/427; 205/781; 205/783.5; 205/785
[58] Field of Search .................................... 204/425, 426, 204/427, 428, 429, 424, 408; 205/784, 784.5, 785, 781, 783.5

[56] References Cited

U.S. PATENT DOCUMENTS

| | | | |
|---|---|---|---|
| 4,909,922 | 3/1990 | Kato et al. | 204/406 |
| 5,236,569 | 8/1993 | Murase et al. | 204/412 |
| 5,672,811 | 9/1997 | Kato et al. | 73/31.05 |
| 5,720,863 | 2/1998 | Kim et al. | 204/406 |
| 5,763,763 | 6/1998 | Kato et al. | 73/23.2 |

FOREIGN PATENT DOCUMENTS 3-167467 7/1991 Japan .
85-00660 2/1985 WIPO .

*Primary Examiner*—Robert J. Warden, Sr.
*Assistant Examiner*—Kaj K. Olsen
*Attorney, Agent, or Firm*—Parkhurst & Wendel, L.L.P.

[57] ABSTRACT

Disclosed is a gas sensor comprising a main pumping cell including a solid electrolyte layer contacting with an external space, and an inner pumping electrode and an outer pumping electrode formed on inner and outer surfaces of the solid electrolyte layer, for pumping-processing oxygen contained in a measurement gas introduced from the external space on the basis of a control voltage applied between the electrodes; a feedback control system for adjusting the control voltage to give a predetermined level of a voltage between the inner pumping electrode and a reference electrode disposed at a reference gas-introducing space; and a heater for heating at least the main pumping cell to a predetermined temperature; wherein the outer pumping electrode is connected to a negative side lead wire of the heater. Accordingly, the control operation in the feedback control system, which is performed to constantly control the concentration of a predetermined gas component in the measurement gas by the aid of the pumping operation, is not affected by the heater leak current, the length of the heater lead wire, and the heater current (heater output). Thus, it is possible to accurately control the concentration of the predetermined gas component.

11 Claims, 6 Drawing Sheets

PRIOR ART 5,976,335

GAS SENSOR HAVING A FUNCTION FOR MINIMIZING HEATER LEAK CURRENT

BACKGROUND OF THE INVENTION

1. Field of the Invention

The present invention relates to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm.

2. Description of the Related Art

In recent years, exhaust gas, which is discharged from vehicles or automobiles such as gasoline-fueled automobiles and diesel powered automobiles, contains nitrogen oxides (NOx) such as nitrogen monoxide (NO) and nitrogen dioxide ($NO_2$), as well as carbon monoxide (CO), carbon dioxide ($CO_2$), water ($H_2O$), hydrocarbon (HC), hydrogen ($H_2$), oxygen ($O_2$) and so on. In such exhaust gas, about 80% of the entire NOx is occupied by NO, and about 95% of the entire NOx is occupied by NO and $NO_2$.

The three way catalyst, which is used to clean HC, CO, and NOx contained in the exhaust gas, exhibits its maximum cleaning efficiency in the vicinity of the theoretical air fuel ratio (A/F=14.6). If A/F is controlled to be not less than 16, the amount of produced NOx is decreased. However, the cleaning efficiency of the catalyst is lowered, and consequently the amount of discharged NOx is apt to increase.

Recently, in order to effectively utilize fossil fuel and avoid global warming, the market demand increases, for example, in that the discharge amount of $CO_2$ should be suppressed. In order to respond to such a demand, it becomes more necessary to improve the fuel efficiency. In response to such a demand, for example, the lean burn engine and the catalyst for cleaning NOx are being researched. Especially, the need for a NOx sensor increases.

A conventional NOx analyzer has been hitherto known as an instrument for detecting NOx. The conventional NOx analyzer is operated to measure a characteristic inherent in NOx, based on the use of chemical luminous analysis. However, the conventional NOx analyzer is inconvenient in that the instrument itself is extremely large and expensive.

The conventional NOx analyzer requires frequent maintenance because optical parts are used to detect NOx. Further, when the conventional NOx analyzer is used, any sampling operation should be performed for measurement of NOx, wherein it is impossible to directly insert a detecting element itself into a fluid. Therefore, the conventional NOx analyzer is not suitable for analyzing transient phenomena such as those occur in the exhaust gas discharged from an automobile, in which the condition frequently varies.

In order to dissolve the inconveniences as described above, there has been suggested a sensor for measuring a desired gas component in exhaust gas by using a substrate composed of an oxygen ion-conductive solid electrolyte.

The suggested conventional gas sensor is exemplified by an all-range type oxygen sensor as shown in FIG. 7. Another type of a gas sensor for measuring gas (for example, NOx) having bound oxygen is also known, in which the oxygen concentration in the gas is lowered to be at a certain low level by using an oxygen pump, and then the oxygen concentration is further lowered to decompose NOx so that oxygen produced during the decomposition is measured by using an oxygen pump to measure NOx.

For example, the gas sensor shown in FIG. 7 will be explained. The gas sensor comprises an internal space 2 for introducing a measurement gas from an external space thereinto, a space (reference gas-introducing space) 4 for introducing a reference gas, for example, atmospheric air to be used as a reference for measuring oxides, and an oxygen pump 6 for maintaining a constant partial pressure of oxygen in the internal space 2.

The oxygen pump 6 comprises an inner pumping electrode 8 provided on the side of the internal space 2, an outer pumping electrode 10 provided on the side of the external space, and an oxygen ion-conductive solid electrolyte layer 12 existing between the both electrodes 8, 10. A reference electrode 14 is provided in the reference gas-introducing space 4.

The gas sensor performs feedback control for a control voltage Vp0 to be applied to the oxygen pump 6 so as to maintain a constant voltage of electromotive force (detection voltage V0) generated between the inner pumping electrode 8 and the reference electrode 14.

When the temperature of exhaust gas greatly changes as in automobiles, the gas sensor is provided with a heater 16 together with a mechanism provided for controlling electric power to be supplied to the heater 16.

In the conventional gas sensor, as shown in FIG. 7, in order to avoid oscillation of the feedback control system 18 concerning the oxygen pump 6, the inner pumping electrode 8 of the oxygen pump 6 is connected to a lead wire (GND) disposed on the negative side of the heater 16 to make a short circuit (see, for example, Japanese Laid-Open Patent Publication No. 3-167467).

However, when the wiring is arranged as described above, oxygen is moved from the inner pumping electrode 8 toward the heater 16 due to a leak current (heater leak current) from the lead wire of the heater 16.

That is, in the case of the conventional gas sensor, it is feared that the oxygen concentration in the internal space 2 is affected by the heater leak current, and the oxygen pump 6 fails to accurately control the oxygen concentration in the internal space 2.

When the current flowing through the heater 16 is large, the electromotive force, which is generated by the resistance of the lead wire of the heater 16, cannot be neglected. For example, assuming that a lead wire having a length of 3 m has a resistance value of 0.1 Ω, when a heater current of 1 A is allowed to flow through the lead wire, an electromotive force (voltage) of "resistance value of lead wire x heater current=100 mV" is generated in the lead wire.

Therefore, the electromotive force is superimposed on the detection voltage V0 in the feedback control system 18, causing a problem that it is impossible to accurately control the control voltage Vp0 to be applied to the oxygen pump 6.

As described above, in the case of the conventional gas sensor, it is feared that the oxygen concentration in the internal space 2 cannot be controlled accurately, because the detection voltage V0 is affected by the length of the lead wire and the heater current (heater output), in the feedback control system 18 for the oxygen pump 6.

SUMMARY OF THE INVENTION

The present invention has been made taking the foregoing problem into consideration, an object of which is to provide a gas sensor comprising a feedback control system for constantly controlling the concentration of a predetermined gas component contained in a measurement gas by the aid of the pumping operation, in which the control operation performed by the feedback control system is not affected by the heater leak current, the length of the heater lead wire, and the heater current (heater output), making it possible to accurately control the concentration of the predetermined gas component.

In order to achieve the object as described above, the present invention provides a gas sensor comprising a main pumping means including a solid electrolyte contacting with an external space, and an inner pumping electrode and an outer pumping electrode formed on inner and outer surfaces of the solid electrolyte, for pumping-processing a predetermined gas component contained in a measurement gas introduced from the external space on the basis of a control voltage applied between the electrodes; a feedback control system for adjusting the control voltage to give a predetermined level of a voltage between the inner pumping electrode of the main pumping means and a reference electrode disposed at a reference gas-introducing portion; and a heater for heating at least the main pumping means to a predetermined temperature; wherein the outer pumping electrode of the main pumping means is connected to a ground side lead wire of the heater.

According to the present invention, at first, the predetermined gas component contained in the measurement gas introduced from the external space is subjected to pumping processing effected by the main pumping means. During this process, the predetermined gas component is adjusted to have a predetermined concentration as a result of adjustment performed by the feedback control system for the control voltage. Specifically, the control voltage is adjusted by the feedback control system so as to give the predetermined level of the voltage between the inner pumping electrode of the main pumping means and the reference electrode disposed at the reference gas-introducing portion. Thus, the concentration of the predetermined gas component is adjusted to be a concentration corresponding to the predetermined level.

When the pumping amount of the predetermined gas component processed by the main pumping means is changed, and the concentration of the predetermined gas component in the measurement gas is changed, then the terminal voltage between the inner electrode and the reference electrode is changed without any time delay. Accordingly, the oscillation phenomenon does not occur in the feedback control.

The pumping operation is performed while the main pumping means is heated to the predetermined temperature by the heater. Therefore, the concentration of the predetermined gas component contained in the measurement gas is adjusted with a high degree of accuracy.

Especially, in the gas sensor according to the present invention, the outer pumping electrode of the main pumping means is connected to the ground side lead wire of the heater. Accordingly, oxygen is not moved from the inner pumping electrode toward the heater.

In the present invention, the voltage between the inner pumping electrode and the reference electrode is a voltage corresponding to the concentration of the predetermined gas component during the pumping processing effected by the main pumping means, i.e., the detection voltage. Moreover, the inner pumping electrode is not connected to the heater lead wire. Therefore, no phenomenon occurs, in which the electromotive force (voltage) associated with the resistance of the lead wire and the heater current is superimposed on the detection voltage.

As described above, in the gas sensor according to the present invention, the feedback control system, which constantly controls the concentration of the predetermined gas component in the measurement gas by the aid of the pumping operation, is operated such that the control operation effected in the feedback control system is not affected by the heater leak current, the length of the heater lead wire, and the heater current (heater output). Thus, it is possible to accurately control the concentration of the predetermined gas component.

Preferably, the gas sensor constructed as described above may further comprise a measuring pumping means including a solid electrolyte and a detecting electrode formed on the solid electrolyte, for pumping-processing the predetermined gas component contained in the measurement gas after being pumping-processed by the main pumping means, on the basis of a voltage applied between the detecting electrode and the reference electrode; and a current-detecting means for detecting a pumping current generated depending on an amount of the predetermined gas component pumping-processed by the measuring pumping means.

Accordingly, the measurement gas, which has been adjusted for the concentration of the predetermined gas component by the main pumping means, is introduced into the measuring pumping means in the next step. The measuring pumping means pumping-processes the predetermined gas component contained in the measurement gas, on the basis of the voltage applied between the detecting electrode and the reference electrode. The pumping current, which is generated in the measuring pumping means depending on the amount of the predetermined gas component pumping-processed by the measuring pumping means, is detected by the current-detecting means. The amount of the specified component in the measurement gas is determined on the basis of the detected value.

Preferably, the gas sensor constructed as described above may further comprise a concentration-detecting means including a solid electrolyte and a detecting electrode formed on the solid electrolyte, for generating an electromotive force corresponding to a difference between an amount of the predetermined gas component contained in the measurement gas after being pumping-processed by the main pumping means and an amount of the predetermined gas component contained in a reference gas existing on a side of the reference electrode; and a voltage-detecting means for detecting the electromotive force generated by the concentration-detecting means.

Accordingly, the measurement gas, which has been adjusted for the concentration of the predetermined gas component by the main pumping means, is introduced into the concentration-detecting means in the next step. The main pumping means generates the electromotive force corresponding to the difference between the amount of the predetermined gas component contained in the measurement gas after being pumping-processed by the main pumping means and the amount of the predetermined gas component contained in the reference gas existing on the side of the reference electrode.

The electromotive force is detected by the voltage-detecting means located downstream. The amount of the specified component in the measurement gas is determined on the basis of the detected value.

Preferably, the gas sensor constructed as described above may further comprise an auxiliary feedback control system for adjusting the concentration of the predetermined gas component contained in the measurement gas to be a constant concentration during the pumping process effected by the main pumping means. This feedback control system is realized, for example, by an arrangement to make adjustment so that a voltage between the auxiliary pumping electrode formed in the vicinity of the detecting electrode and the reference electrode is at a predetermined level.

Accordingly, at first, the measurement gas, which has been subjected to coarse adjustment for the predetermined gas component to have the predetermined concentration by the aid of the main pumping means, is further subjected to fine adjustment for the concentration of the predetermined gas component by the aid of the auxiliary pumping means. During the period in which the foregoing operation is performed, when the concentration of the predetermined gas component in the measurement gas in the external space is greatly changed (for example, oxygen concentration is changed from 0 to 20%), then the concentration distribution of the predetermined gas component in the measurement gas introduced into the main pumping means is greatly changed, and the amount of the predetermined gas component introduced into the measuring pumping means or the concentration-detecting means is also changed.

The concentration of the predetermined gas component in the measurement gas after being pumping-processed by the main pumping means is finely adjusted by the pumping process effected by the auxiliary pumping means. However, owing to the pumping process performed by the main pumping means, the change in concentration of the predetermined gas component in the measurement gas introduced into the auxiliary pumping means is greatly reduced as compared with the change in concentration of the predetermined gas component in the measurement gas from the external space (measurement gas introduced into the main pumping means). Accordingly, it is possible to accurately and constantly control the concentration of the predetermined gas component in the vicinity of the detecting electrode of the measuring pumping means or in the vicinity of the detecting electrode of the concentration-detecting means.

Therefore, the concentration of the predetermined gas component introduced into the measuring pumping means or the concentration-detecting means is scarcely affected by the change in concentration of the predetermined gas component in the measurement gas (measurement gas introduced into the main pumping means). As a result, the pumping current value detected by the current-detecting means or the electromotive force detected by the voltage-detecting means is not affected by the change in concentration of the predetermined gas component in the measurement gas, which has a value accurately corresponding to the amount of the objective component existing in the measurement gas.

The main pumping means may comprise the inner pumping electrode and the outer pumping electrode formed at the inside and outside of a first chamber surrounded by substrates composed of solid electrolytes for introducing the measurement gas thereinto, and the substrate interposed between the both electrodes.

The measuring pumping means may comprise the detecting electrode formed at the inside of a second chamber surrounded by substrates composed of solid electrolytes for introducing the measurement gas after being pumping-processed by the main pumping means thereinto, the reference electrode formed in a reference gas-introducing chamber surrounded by substrates composed of solid electrolytes for introducing a reference gas thereinto, and the substrate interposed between the detecting electrode and the reference electrode.

The concentration-detecting means may comprise the detecting electrode formed at the inside of a second chamber surrounded by substrates composed of solid electrolytes for introducing the measurement gas after being pumping-processed by the main pumping means thereinto, the reference electrode formed in a reference gas-introducing chamber surrounded by substrates composed of solid electrolytes for introducing a reference gas thereinto, and the substrate interposed between the detecting electrode and the reference electrode.

Preferably, the gas sensor constructed as described above may further comprise a first diffusion rate-determining section provided at a passage to introduce the measurement gas from the external space into the first chamber, for giving a predetermined diffusion resistance to the measurement gas, and a second diffusion rate-determining section provided at a passage to introduce the measurement gas after being pumping-processed by the main pumping means into the second chamber, for giving a predetermined diffusion resistance to the measurement gas.

Preferably, the gas sensor may further comprise a third diffusion rate-determining section provided at a passage for the measurement gas to enter the detecting electrode in the second chamber, for giving a predetermined diffusion resistance to the measurement gas.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Explanation will be made below with reference to FIGS. 1 to 6 for several illustrative embodiments in which the gas sensor according to the present invention is applied to gas sensors for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm.

Figure 1:
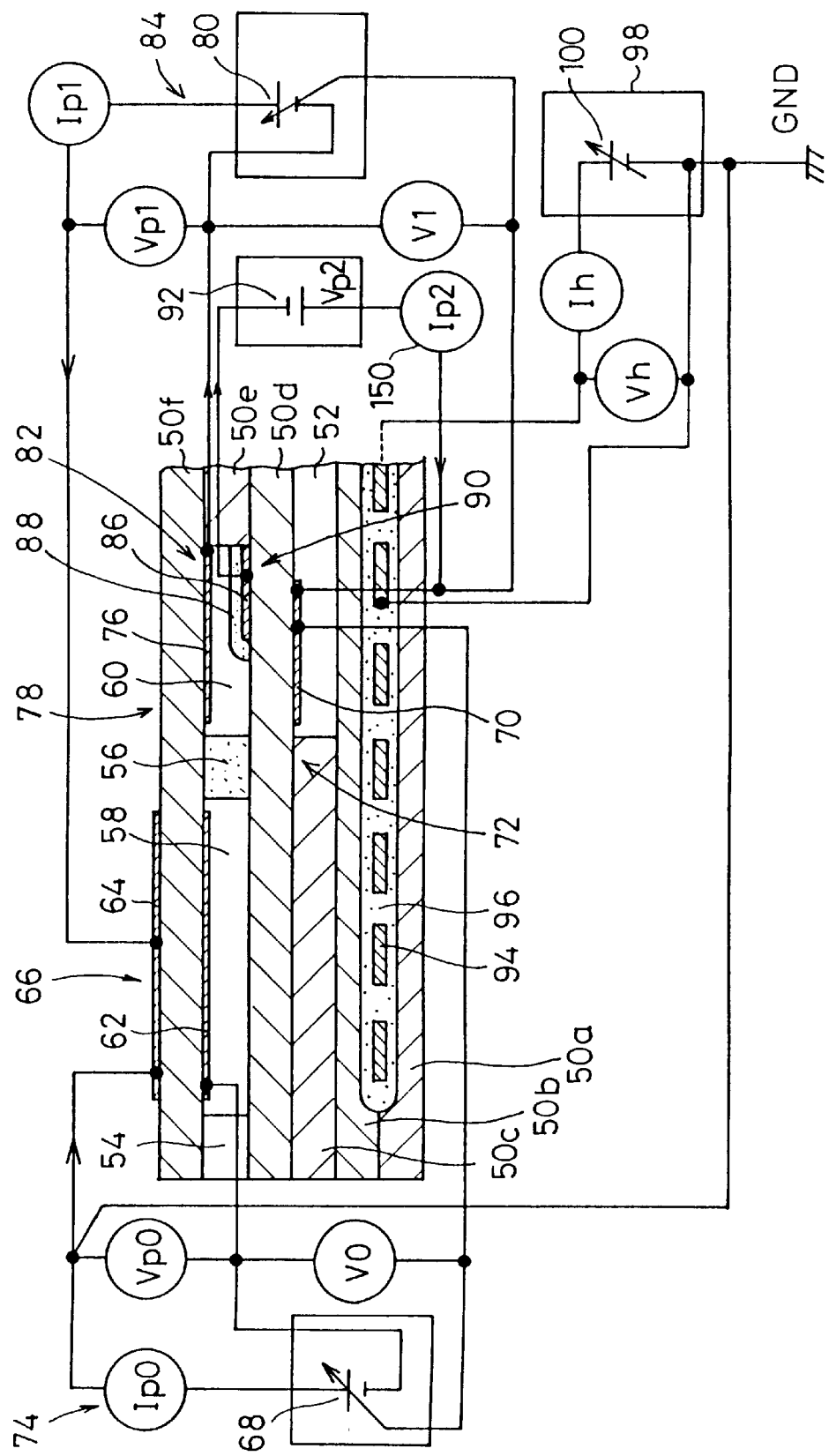
FIG. 1 shows an arrangement of a gas sensor according to a first embodiment.

At first, as shown in FIG. 1, a gas sensor according to the first embodiment comprises, for example, six stacked solid electrolyte layers 50a to 50f composed of ceramics based on the use of oxygen ion-conductive solid electrolytes such as $ZrO_2$. First and second layers from the bottom are designated as first and second substrate layers 50a, 50b respectively. Third and fifth layers from the bottom are designated as first and second spacer layers 50c, 50e respectively. Fourth and sixth layers from the bottom are designated as first and second solid electrolyte layers 50d, 50f respectively.

Specifically, the first spacer layer 50c is stacked on the second substrate layer 50b. The first solid electrolyte layer 50d, the second spacer layer 50e, and the second solid electrolyte layer 50f are successively stacked on the first spacer layer 50c.

A space (reference gas-introducing space) 52, into which a reference gas such as atmospheric air to be used as a reference for measuring oxides is introduced, is formed between the second substrate layer 50b and the first solid electrolyte layer 50d, the space 52 being comparted by a lower surface of the first solid electrolyte layer 50d, an upper surface of the second substrate layer 50b, and side surfaces of the first spacer layer 50c.

The second spacer layer 50e is interposed between the first and second solid electrolyte layers 50d, 50f. First and second diffusion rate-determining sections 54, 56 are also interposed between the first and second solid electrolyte layers 50d, 50f.

A first chamber 58 for adjusting the partial pressure of oxygen in a measurement gas is formed and comparted by a lower surface of the second solid electrolyte layer 50f, side surfaces of the first and second diffusion rate-determining sections 54, 56, and an upper surface of the first solid electrolyte layer 50d. A second chamber 60 for finely adjusting the partial pressure of oxygen in the measurement gas and measuring oxides, for example, nitrogen oxides (NOx) in the measurement gas is formed and comparted by a lower surface of the second solid electrolyte layer 50f, a side surface of the second diffusion rate-determining section 56, a side surface of the second spacer layer 50e, and an upper surface of the first solid electrolyte layer 50d.

The external space communicates with the first chamber 58 via the first diffusion-rate determining section 54, and the first chamber 58 communicates with the second chamber 60 via the second diffusion rate-determining section 56.

The first and second diffusion-rate determining sections 54, 56 give predetermined diffusion resistances to the measurement gas to be introduced into the first and second chambers 58, 60 respectively. Each of the first and second diffusion-rate determining sections 54, 56 can be formed as a passage composed of, for example, a porous material, or a small hole having a predetermined cross-sectional area so that the measurement gas may be introduced.

Especially, the second diffusion-rate determining section 56 is arranged and filled with a porous material comprising, for example, $ZrO_2$. Preferably, the diffusion resistance of the second diffusion-rate determining section 56 is made larger than the diffusion resistance of the first diffusion-rate determining section 54. However, no problem occurs even when the former is smaller than the latter.

The atmosphere in the first chamber 58 is introduced into the second chamber 60 under the predetermined diffusion resistance via the second diffusion rate-determining section 56.

An inner pumping electrode 62 having a substantially rectangular planar configuration and composed of a porous cermet electrode is formed on the entire lower surface portion for forming the first chamber 58, of the lower surface of the second solid electrolyte layer 50f. An outer pumping electrode 64 is formed on a portion corresponding to the inner pumping electrode 62, of the upper surface of the second solid electrolyte layer 50f. An electrochemical pumping cell, i.e., a main pumping cell 66 is constructed by the inner pumping electrode 62, the outer pumping electrode 64, and the second solid electrolyte layer 50f interposed between the both electrodes 62, 64.

A desired control voltage (pumping voltage) Vp0 is applied between the inner pumping electrode 62 and the outer pumping electrode 64 of the main pumping cell 66 by the aid of an external variable power source 68 to allow a pumping current Ip0 to flow in a positive or negative direction between the outer pumping electrode 64 and the inner pumping electrode 62. Thus, the oxygen in the atmosphere in the first chamber 58 can be pumped out to the external space, or the oxygen in the external space can be pumped into the first chamber 58.

A reference electrode 70 is formed on a portion exposed to the reference gas-introducing space 52, of the lower surface of the first solid electrolyte layer 50d. An electrochemical sensor cell, i.e., an oxygen partial pressure-detecting cell 72 is constructed by the inner pumping electrode 62, the reference electrode 70, the second solid electrolyte layer 50f, the second spacer layer 50e, and the first solid electrolyte layer 50d.

An electromotive force is generated between the inner pumping electrode 62 and the reference electrode 70 on the basis of a difference in oxygen concentration between the atmosphere in the first chamber 58 and the reference gas (atmospheric air) in the reference gas-introducing space 52. The oxygen partial pressure-detecting cell 72 makes it possible to detect the partial pressure of oxygen in the atmosphere in the first chamber 58 on the basis of the generated electromotive force.

The detected value of the partial pressure of oxygen is used to feedback-control the variable power source 68. Specifically, the pumping operation performed by the main pumping cell 66 is controlled by the aid of the feedback control system 74 for the main pump so that the partial pressure of oxygen in the atmosphere in the first chamber 58 has a predetermined value which is sufficiently low to control the partial pressure of oxygen in the second chamber 60 in the next step.

The feedback control system 74 includes a circuit which is constructed to perform feedback control for the voltage Vp0 between the outer pumping electrode 64 and the inner pumping electrode 62 so that the difference (detection voltage V0) between the electric potential of the inner pumping electrode 62 and the electric potential of the reference electrode 70 is at a predetermined voltage level. In this embodiment, the inner pumping electrode 62 is subjected to signal level grounding (which is different from earth grounding GND). The electric potential of the signal level grounding is generated, for example, by a DC—DC converter.

Therefore, the main pumping cell 66 pumps out or pumps in oxygen in an amount corresponding to the level of the pumping voltage Vp0, of the measurement gas introduced into the first chamber 58. The oxygen concentration in the first chamber 58 is subjected to feedback control to give a predetermined level by repeating the series of operations described above.

The porous cermet electrode for constructing the inner pumping electrode 62 and the outer pumping electrode 64 is composed of a metal such as Pt and a ceramic such as $ZrO_2$. However, it is necessary, for the inner pumping electrode 62 arranged in the first chamber 58 contacting with the measurement gas, to use a material having a weak reducing ability or no reducing ability with respect to the NO component in the measurement gas. It is preferable that the inner pumping electrode 62 is composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35 vol % of the entire metal components.

On the other hand, an auxiliary pumping electrode 76 having a substantially rectangular planar configuration and composed of a porous cermet electrode is formed on the entire lower surface portion for forming the second chamber 60, of the lower surface of the second solid electrolyte layer 50*f*. An auxiliary electrochemical pumping cell, i.e., an auxiliary pumping cell 78 is constructed by the outer pumping electrode 64 of the main pumping cell 66, the auxiliary pumping electrode 76, and the second solid electrolyte layer 50*f*.

A desired auxiliary control voltage Vp1 is applied between the outer pumping electrode 64 and the auxiliary pumping electrode 76 of the auxiliary pumping cell 78 by the aid of an external auxiliary variable power source 80. Thus, the oxygen in the atmosphere in the second chamber 60 is pumped out to the external space, or the oxygen in the external space is pumped into the second chamber 60.

An electrochemical sensor cell, i.e., an auxiliary oxygen partial pressure-detecting cell 82 is constructed by the auxiliary pumping electrode 76, the reference electrode 70, the second solid electrolyte layer 50*f*, the second spacer layer 50*e*, and the first solid electrolyte layer 50*d*. An electromotive force is generated between the auxiliary pumping electrode 76 and the reference electrode 70 on the basis of a difference in oxygen concentration between the atmosphere in the second chamber 60 and the reference gas (atmospheric air) in the reference gas-introducing space 52. The auxiliary oxygen partial pressure-detecting cell 82 makes it possible to detect the partial pressure of oxygen in the atmosphere in the second chamber 60 on the basis of the generated electromotive force.

The detected value of the partial pressure of oxygen is used to control the auxiliary variable power source 80. Specifically, the pumping operation performed by the auxiliary pumping cell 78 is controlled by the aid of the feedback control system 84 so that the partial pressure of oxygen in the atmosphere in the second chamber 60 has a low value of partial pressure of oxygen which does not substantially affects the measurement for the amount of the objective component under a condition in which the measurement gas component (NOx) is not substantially reduced or decomposed.

The auxiliary feedback control system 84 includes a circuit which is constructed to perform feedback control for the voltage Vp1 (auxiliary control voltage) between the outer pumping electrode 64 and the auxiliary pumping electrode 76 so that the difference (auxiliary detection voltage V1) between the electric potential of the auxiliary pumping electrode 76 and the electric potential of the reference electrode 70 is at a predetermined voltage level.

Therefore, the auxiliary pumping cell 78 pumps out or pumps in oxygen in an amount corresponding to the level of the auxiliary control voltage Vp1, of the measurement gas introduced into the second chamber 60. The oxygen concentration in the second chamber 60 is subjected to feedback control to give a predetermined level by repeating the series of operations described above.

In this embodiment, owing to the operation of the main pumping cell 66 in the first chamber 58, the change in amount of oxygen introduced into the second chamber 60 is greatly reduced as compared with the change in the measurement gas. Accordingly, the partial pressure of oxygen in the second chamber 60 is accurately controlled to be constant.

A detecting electrode 86 having a substantially rectangular planar configuration and composed of a porous cermet electrode is formed at a portion separated from the second diffusion rate-determining section 56, on an upper surface portion for forming the second chamber 60, of the upper surface of the first solid electrolyte layer 50*d*. An alumina film for constructing a third diffusion rate-determining section 88 is formed so that the detecting electrode 86 is covered therewith. An electrochemical pumping cell, i.e., a measuring pumping cell 90 is constructed by the detecting electrode 86, the reference electrode 70, and the first solid electrolyte layer 50*d*.

The detecting electrode 86 is composed of a porous cermet comprising zirconia as a ceramic and Rh as a metal capable of reducing NOx as the measurement gas component. Accordingly, the detecting electrode 86 functions as an NOx-reducing catalyst for reducing NOx existing in the atmosphere in the second chamber 60. Further, the oxygen in the atmosphere in the second chamber 60 can be pumped out to the reference gas-introducing space 52 by applying a constant voltage Vp2 between the detecting electrode 86 and the reference electrode 70 by the aid of a DC power source 92. The pumping current Ip2, which is allowed to flow in accordance with the pumping operation performed by the measuring pumping cell 90, is detected by an ammeter 150.

The constant voltage (DC) power source 92 can apply a voltage of a magnitude to give a limiting current to the pumping for oxygen produced during decomposition in the measuring pumping cell 90 under the inflow of NOx restricted by the third diffusion rate-determining section 88.

The gas sensor according to the first embodiment further comprises a heater 94 for generating heat in accordance with electric power supply from the outside. The heater 94 is embedded in a form of being vertically interposed between the first and second substrate layers 50*a*, 50*b*. The heater 94 is provided in order to increase the conductivity of oxygen ion. A ceramic layer 96 composed of alumina or the like is formed to cover upper and lower surfaces of the heater 94 so that the heater 94 is electrically insulated from the substrate layers 50*a*, 50*b*.

As shown in FIG. 1, the heater 94 is arranged over the entire portion ranging from the first chamber 58 to the second chamber 60. Each of the first chamber 58 and the second chamber 60 is heated to a predetermined temperature in accordance with the control performed by a heater output controller 98 connected to the heater 94. Simultaneously, each of the main pumping cell 66, the oxygen partial pressure-detecting cell 72, the auxiliary pumping cell 78, and the measuring pumping cell 90 is also heated to a predetermined temperature and maintained at that temperature. In this embodiment, a positive side lead wire of the heater 94 is connected to a heater power source 100 via the heater output controller 98, and a negative side lead wire of the heater 94 is subjected to earth grounding GND. The heater current Ih is measured by an ammeter and the heater voltage Vh is measured by a voltmeter.

The gas sensor according to the first embodiment is constructed such that the outer pumping electrode 64 of the main pumping cell 66 is connected to the negative side lead wire of the heater 94.

Next, the operation of the gas sensor according to the first embodiment will be explained. At first, the forward end of the gas sensor is disposed in the external space. Accordingly, the measurement gas is introduced into the first chamber 58 under the predetermined diffusion resistance via the first diffusion rate-determining section 54. The measurement gas, which has been introduced into the first chamber 58, is subjected to the pumping operation for oxygen, caused by applying the predetermined pumping voltage Vp0 between the outer pumping electrode 64 and the inner pumping electrode 62 which construct the main pumping cell 66. The partial pressure of oxygen is controlled to be a predetermined value, for example, $10^{-7}$ atm. The control is performed by the aid of the feedback control system 74.

The first diffusion rate-determining section 54 serves to limit the amount of diffusion and inflow of oxygen in the measurement gas into the measuring space (first chamber 58) when the pumping voltage Vp0 is applied to the main pumping cell 66 so that the current flowing through the main pumping cell 66 is suppressed.

In the first chamber 58, a state of partial pressure of oxygen is established, in which NOx in the atmosphere is not reduced by the inner pumping electrode 62 in an environment of being heated by the external measurement gas and being heated by the heater 94. For example, a condition of partial pressure of oxygen is formed, in which the reaction of NO→$1/2N_2+1/2O_2$ does not occur, because of the following reason. That is, if NOx in the measurement gas (atmosphere) is reduced in the first chamber 58, it is impossible to accurately measure NOx in the second chamber 60 disposed at the downstream. In this context, it is necessary to establish a condition in the first chamber 58 in which NOx is not reduced by the component which participates in reduction of NOx (in this case, the metal component of the inner pumping electrode 62). Specifically, as described above, such a condition is achieved by using, for the inner pumping electrode 62, a material having a low ability to reduce NOx, for example, an alloy of Au and Pt.

The gas in the first chamber 58 is introduced into the second chamber 60 under the predetermined diffusion resistance via the second diffusion rate-determining section 56. The gas, which has been introduced into the second chamber 60, is subjected to the pumping operation for oxygen, caused by applying the auxiliary control voltage Vp1 between the outer pumping electrode 64 and the auxiliary pumping electrode 76 which constitute the auxiliary pumping cell 78 to make fine adjustment so that the partial pressure of oxygen has a constant and low value of partial pressure of oxygen.

The second diffusion rate-determining section 56 serves to limit the amount of diffusion and inflow of oxygen in the measurement gas into the measuring space (second chamber 60) when the control voltage Vp1 is applied to the auxiliary pumping cell 78 so that the pumping current Ip1 flowing through the auxiliary pumping cell 78 is suppressed, in the same manner as performed by the first diffusion rate-determining section 54.

In the second chamber 60, a state of partial pressure of oxygen is also established, in which NOx in the atmosphere is not reduced by the auxiliary pumping electrode 76 in an environment of being heated by the external measurement gas and being heated by the heater 94, in the same manner as in the first chamber 58. Accordingly, it is also necessary for the auxiliary pumping electrode 76 to use a material having a weak reducing ability or no reducing ability with respect to the NO component in the measurement gas, in the same manner as the inner pumping electrode 62. It is preferable that the auxiliary pumping electrode 76 is composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35 vol % of the entire metal components.

The measurement gas, which has been controlled for the partial pressure of oxygen in the second chamber 60 as described above, is introduced into the detecting electrode 86 under the predetermined diffusion resistance via the third diffusion rate-determining section 88.

When it is intended to control the partial pressure of oxygen in the atmosphere in the first chamber 58 to have a low value of the partial pressure of oxygen which does not substantially affect the measurement of NOx, by operating the main pumping cell 66, in other words, when the pumping voltage Vp0 of the variable power source 68 is adjusted by the aid of the feedback control system 74 so that the voltage V0 detected by the oxygen partial pressure-detecting cell 72 is constant, if the oxygen concentration in the measurement gas greatly changes, for example, in a range of 0 to 20%, then the respective partial pressures of oxygen in the atmosphere in the second chamber 60 and in the atmosphere in the vicinity of the detecting electrode 86 slightly change in ordinary cases. This phenomenon is caused probably because of the following reason. That is, when the oxygen concentration in the measurement gas increases, the distribution of the oxygen concentration occurs in the widthwise direction and the thickness direction in the first chamber 58. The distribution of the oxygen concentration changes depending on the oxygen concentration in the measurement gas.

However, in the case of the gas sensor according to the first embodiment, the auxiliary pumping cell 78 is provided for the second chamber 60 so that the partial pressure of oxygen in its internal atmosphere always has a constant low value of the partial pressure of oxygen. Accordingly, even when the partial pressure of oxygen in the atmosphere introduced from the first chamber 58 into the second chamber 60 changes depending on the oxygen concentration in the measurement gas, the partial pressure of oxygen in the atmosphere in the second chamber 60 can be always made to have a constant low value, owing to the pumping operation performed by the auxiliary pumping cell 78. As a result, the partial pressure of oxygen can be controlled to have a low value at which the measurement of NOx is not substantially affected.

NOx in the measurement gas introduced into the detecting electrode 86 is reduced or decomposed around the detecting electrode 86. Thus, for example, a reaction of NO→$1/2N_2+1/2O_2$ is allowed to occur. In this process, a predetermined voltage Vp2, for example, 430 mV (700° C.) is applied between the detecting electrode 86 and the reference electrode 70 for constructing the measuring pumping cell 90, in a direction to pump out the oxygen from the second chamber 60 to the reference gas-introducing space 52.

Therefore, the pumping current Ip2 flowing through the measuring pumping cell 90 has a value which is proportional to a sum of the oxygen concentration in the atmosphere introduced into the second chamber 60, i.e., the oxygen concentration in the second chamber 60 and the oxygen concentration produced by reduction or decomposition of NOx by the aid of the detecting electrode 86.

In this embodiment, the oxygen concentration in the atmosphere in the second chamber 60 is controlled to be constant by means of the auxiliary pumping cell 78. Accordingly, the pumping current Ip2 flowing through the measuring pumping cell 90 is proportional to the NOx concentration. The NOx concentration corresponds to the amount of diffusion of NOx limited by the third diffusion rate-determining section 88. Therefore, even when the oxygen concentration in the measurement gas greatly changes, it is possible to accurately measure the NOx concentration, based on the use of the measuring pumping cell 90 by the aid of the ammeter.

It is assumed, for example, that the partial pressure of oxygen in the atmosphere in the second chamber 60 controlled by the auxiliary pumping cell 78 is 0.02 ppm, and the concentration of NO as the NOx component in the measurement gas is 100 ppm. The pumping current Ip2 flows in an amount corresponding to a sum (=50.02 ppm) of an oxygen concentration of 50 ppm produced by reduction or decomposition of NO and the oxygen concentration of 0.02 ppm in the atmosphere in the second chamber 60. Therefore, almost all of the pumping current value obtained by operating the measuring pumping cell 90 represents the amount brought about by the reduction or decomposition of NO. Accordingly, the obtained result does not depend on the oxygen concentration in the measurement gas.

Now, three illustrative experiments will be described. The illustrative experiments were performed by preparing Example concerning a gas sensor constructed in the same manner as the gas sensor according to the first embodiment, and Comparative Example concerning a gas sensor constructed similarly to the gas sensor according to the first embodiment but including the inner pumping electrode 62 connected to the negative side lead wire of the heater 94.

In the first illustrative experiment, observation was made for the influence of the leak current from the heater 94, exerted on the pumping current Ip0 flowing through the main pumping cell 66, concerning Example and Comparative Example. The first illustrative experiment was performed by setting the oxygen concentration in the external space to be 5%.

Figure 2:
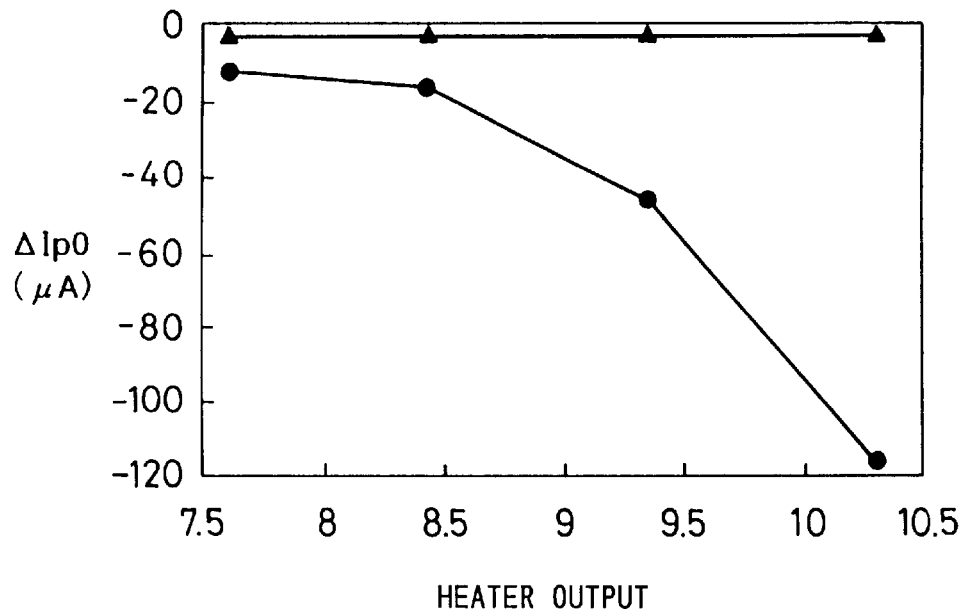
FIG. 2 shows characteristic curves which represent dependency of the difference in pumping current on the heater output, concerning Example and Comparative Example in a first illustrative experiment to investigate the influence of the heater leak current on the pumping current.

FIG. 2 shows experimental results obtained in the first illustrative experiment. Characteristic curves shown in FIG. 2 were obtained by plotting output data obtained in Example and Comparative Example, while giving the heater output (represented by the degree) along the axis of abscissa and the amount of difference ΔIp0 ($\mu$A) in pumping current Ip0 along the axis of ordinate. In FIG. 2, solid triangles represent the experimental result obtained in Example, and solid circles represent the experimental result obtained in Comparative Example.

According to the experimental results, in the case of Comparative Example, when the value obtained at a heater output=7.6 is used as a reference, the difference at a heater output=8.4 is about 5 $\mu$A. However, the differences at heater outputs=9.3 and 10.3 are 35 $\mu$A and 105 $\mu$A respectively. Therefore, the amount of difference increases exponentially as the heater output increases. According to this result, it is understood that the pumping current Ip0 is extremely greatly affected by the leak current of the heater 94 in Comparative Example.

On the contrary, the amount of difference ΔIp0 is maintained to be −5 $\mu$A (constant) over a range of heater outputs=7.6 to 10.3. Accordingly, it is understood that the pumping current Ip0 is scarcely affected by the leak current of the heater 94.

Next, in the second illustrative experiment, observation was made for the influence of the leak current from the heater 94, exerted on the pumping current Ip0 flowing through the main pumping cell 66, concerning Example and Comparative Example, in the same manner as the first illustrative experiment. The second illustrative experiment was performed by setting the oxygen concentration in the external space to be constant (in atmospheric air).

Figure 3:
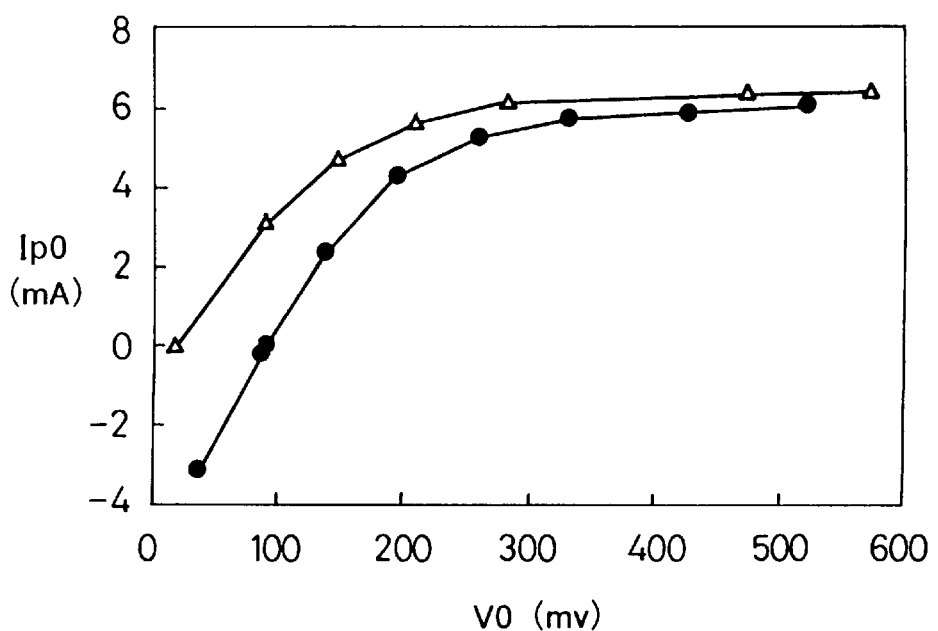
FIG. 3 shows characteristic curves which represent dependency of the pumping current on the detection voltage, concerning Example and Comparative Example in a second illustrative experiment to investigate the influence of the heater leak current on the pumping current.

FIG. 3 shows experimental results obtained in the second illustrative experiment. Characteristic curves shown in FIG. 3 were obtained by plotting output characteristics obtained in Example and Comparative Example, while giving the detection voltage V0 along the axis of abscissa and the pumping current Ip0 along the axis of ordinate. In FIG. 3, triangles represent the output characteristic obtained in Example, and solid circles represent the output characteristic obtained in Comparative Example.

According to the experimental results, in the case of Comparative Example, even when the detection voltage V0 is 0 mV, i.e., even when the oxygen concentration in the first chamber 58 is approximately the same as the oxygen concentration in the reference gas-introducing space 52, the pumping current Ip0 flows. Therefore, it is understood that the pumping current Ip0 is affected by the leak current of the heater 94.

On the contrary, in the case of Example, when the detection voltage is 0 mV, the pumping current Ip0 is also 0 mA. Accordingly, it is understood that the pumping current Ip0 is not affected by the leak current of the heater 94.

Next, in the third illustrative experiment, observation was made for the influence of the length of the lead wire (resistance of the lead wire), exerted on the detection voltage V0, concerning Example and Comparative Example.

Figure 4:
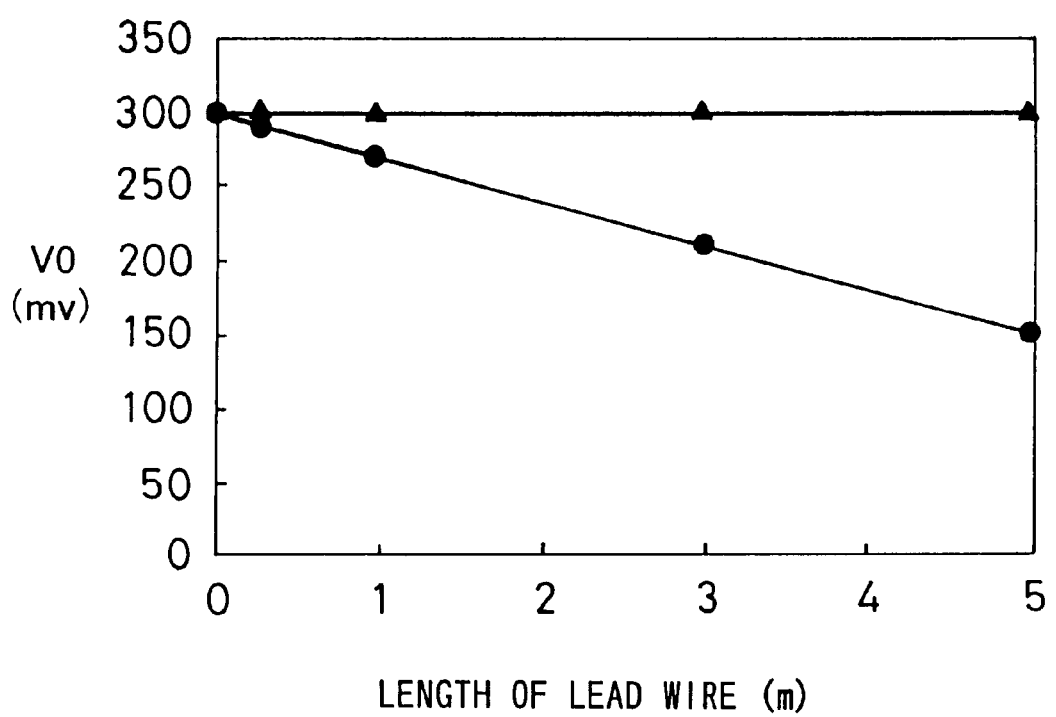
FIG. 4 shows characteristic curves which represent dependency of the detection voltage on the lead wire length (lead wire resistance), concerning Example and Comparative Example in a third illustrative experiment to investigate the influence on the detection voltage exerted by the lead wire length (lead wire resistance).

FIG. 4 shows experimental results obtained in the third illustrative experiment. Characteristic curves shown in FIG. 4 were obtained by plotting output data obtained in Example and Comparative Example, while giving the length of the lead wire (m) along the axis of abscissa and the detection voltage V0 (mV) along the axis of ordinate. In FIG. 4, solid triangles represent the output characteristic obtained in Example, and solid circles represent the output characteristic obtained in Comparative Example. In the third illustrative experiment, the negative side terminal of the reference power source is subjected to earth grounding GND, for making comparison with the detection voltage V0.

According to the experimental results, in the case of Comparative Example, the detection voltage V0 is decreased as the length of the lead wire becomes long. Therefore, it is understood that the detection voltage V0 is extremely greatly affected by the lead wire length of the heater 94.

The reason for this fact is as follows. That is, in the case of Comparative Example, the total voltage of the electromotive force (voltage) generated in the negative side lead wire and the detection voltage V0 generated between the reference electrode 70 and the inner pumping electrode 62 appears between the reference electrode 70 and the earth grounding GND. Therefore, the voltage, which is compared with the voltage (reference voltage) of the reference power source in the feedback control system 74, is not the detection voltage V0, but the total voltage described above.

Therefore, the electromotive force (voltage) generated in the negative side lead wire is increased as the length of the lead wire becomes long, in accordance with which the detection voltage V0 is controlled by the feedback control system 74 to give a voltage as obtained by subtracting the electromotive force from the reference voltage.

On the contrary, in the case of Example, the detection voltage V0 is constant regardless of the length of the lead wire, as also understood from the experimental result shown in FIG. 4. Therefore, the detection voltage V0 is scarcely affected by the length of the lead wire of the heater 94.

As described above, in the gas sensor according to the first embodiment, the outer pumping electrode 64 of the main pumping cell 66 is connected to the negative side lead wire of the heater 94. Accordingly, the oxygen is not moved from the inner pumping electrode 62 toward the heater 94.

In the first embodiment, the voltage V0 between the inner pumping electrode 62 and the reference electrode 70 is the voltage corresponding to the oxygen concentration during the pumping processing effected by the main pumping cell 66, i.e., the detection voltage V0. Moreover, the inner pumping electrode 62 is not connected to the lead wire of the heater 94. Accordingly, no phenomenon occurs, in which the detection voltage V0 is superimposed by the electromotive force (voltage) associated with the resistance R of the lead wire and the heater current.

Therefore, in the gas sensor according to the first embodiment, the feedback control system 74 for constantly controlling the concentration of oxygen in the measurement gas by means of the pumping operation is operated as follows. That is, the control operation effected by the feedback control system 74 is not affected by the leak current of the heater, the length of the lead wire, and the heater current (heater output). Thus, it is possible to accurately control the oxygen concentration.

Figure 5:
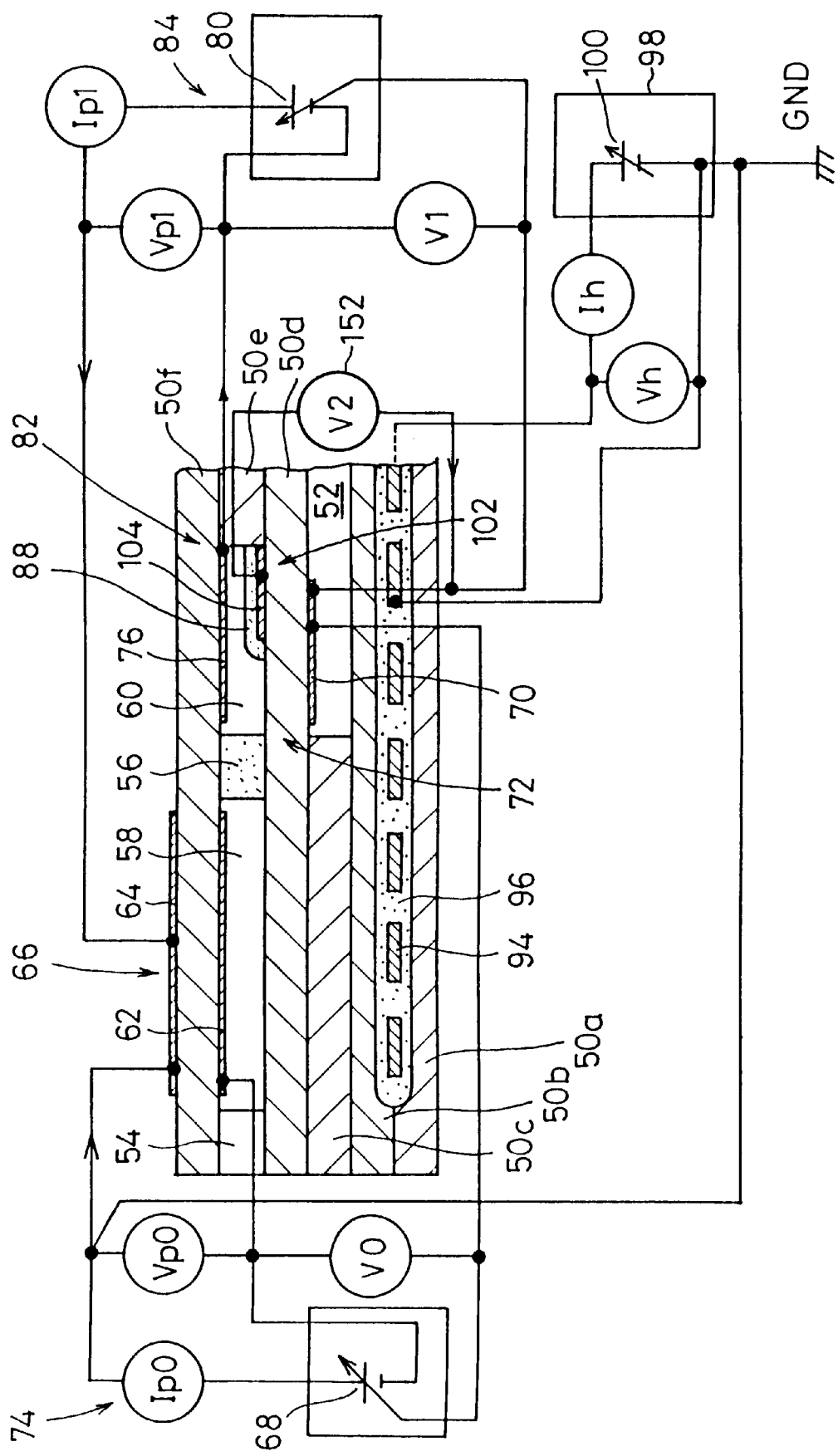
FIG. 5 shows an arrangement of a gas sensor according to a second embodiment.

Next, a gas sensor according to the second embodiment will be explained with reference to FIG. 5. Components or parts corresponding to those shown in FIG. 1 are designated by the same reference numerals, duplicate explanation of which will be omitted.

The gas sensor according to the second embodiment is constructed in approximately the same manner as the gas sensor according to the first embodiment. However, as shown in FIG. 5, the former is different from the latter in that a partial oxygen pressure-detecting cell 102 is provided in place of the measuring pumping cell 90.

The oxygen partial pressure-detecting cell 102 comprises a detecting electrode 104 formed on the upper surface portion for forming the second chamber 60, of the upper surface of the first solid electrolyte layer 50$d$, the reference electrode 70 formed on the lower surface of the first solid electrolyte layer 50$d$, and the first solid electrolyte layer 50$d$ interposed between the both electrodes 104, 70.

In this embodiment, an electromotive force (electromotive force of the oxygen concentration cell) V2 as measured by voltmeter 152, which corresponds to the difference in oxygen concentration between the atmosphere around the detecting electrode 104 and the atmosphere around the reference electrode 70, is generated between the detecting electrode 104 and the reference electrode 70 of the oxygen partial pressure-detecting cell 102.

Therefore, the partial pressure of oxygen in the atmosphere around the detecting electrode 104, in other words, the partial pressure of oxygen defined by the oxygen produced by reduction or decomposition of the measurement gas component (NOx) is detected as a voltage value by measuring the electromotive force (voltage) V2 generated between the detecting electrode 104 and the reference electrode 70 by using a voltmeter.

Figure 6:
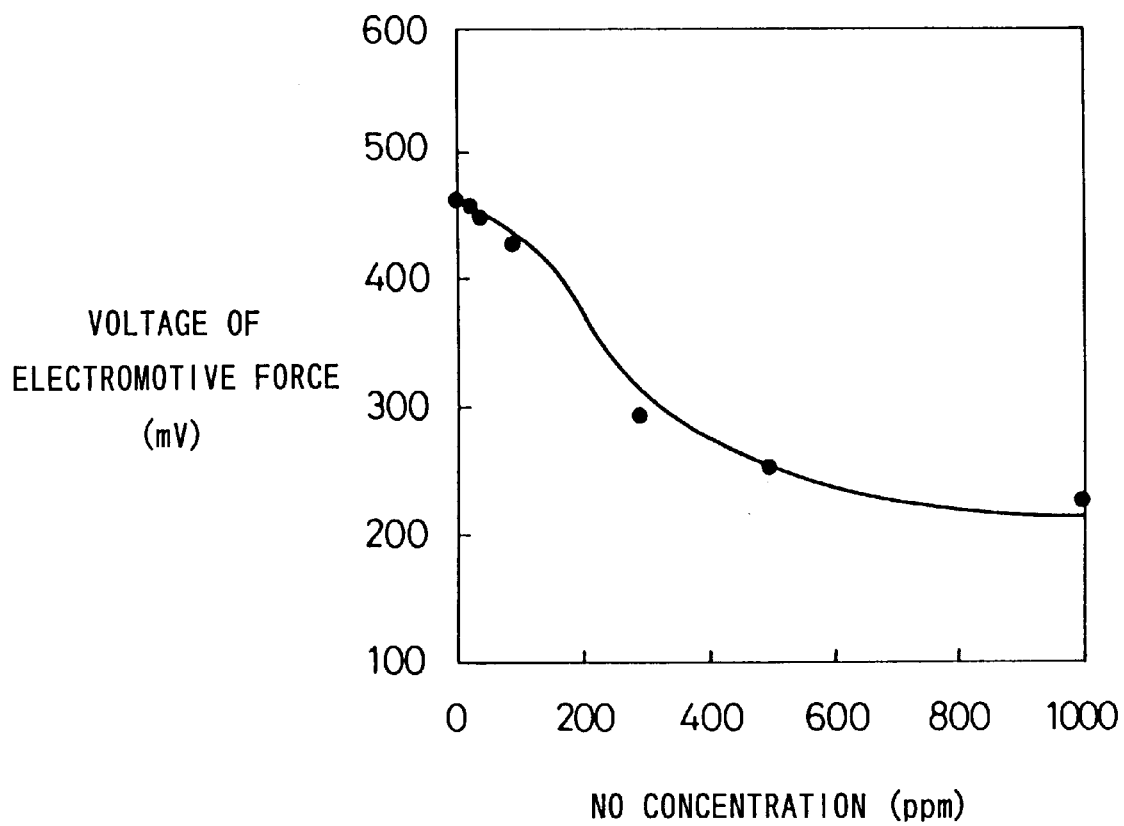
FIG. 6 shows a characteristic curve which represents an output characteristic of the gas sensor according to the second embodiment.
Figure 7:
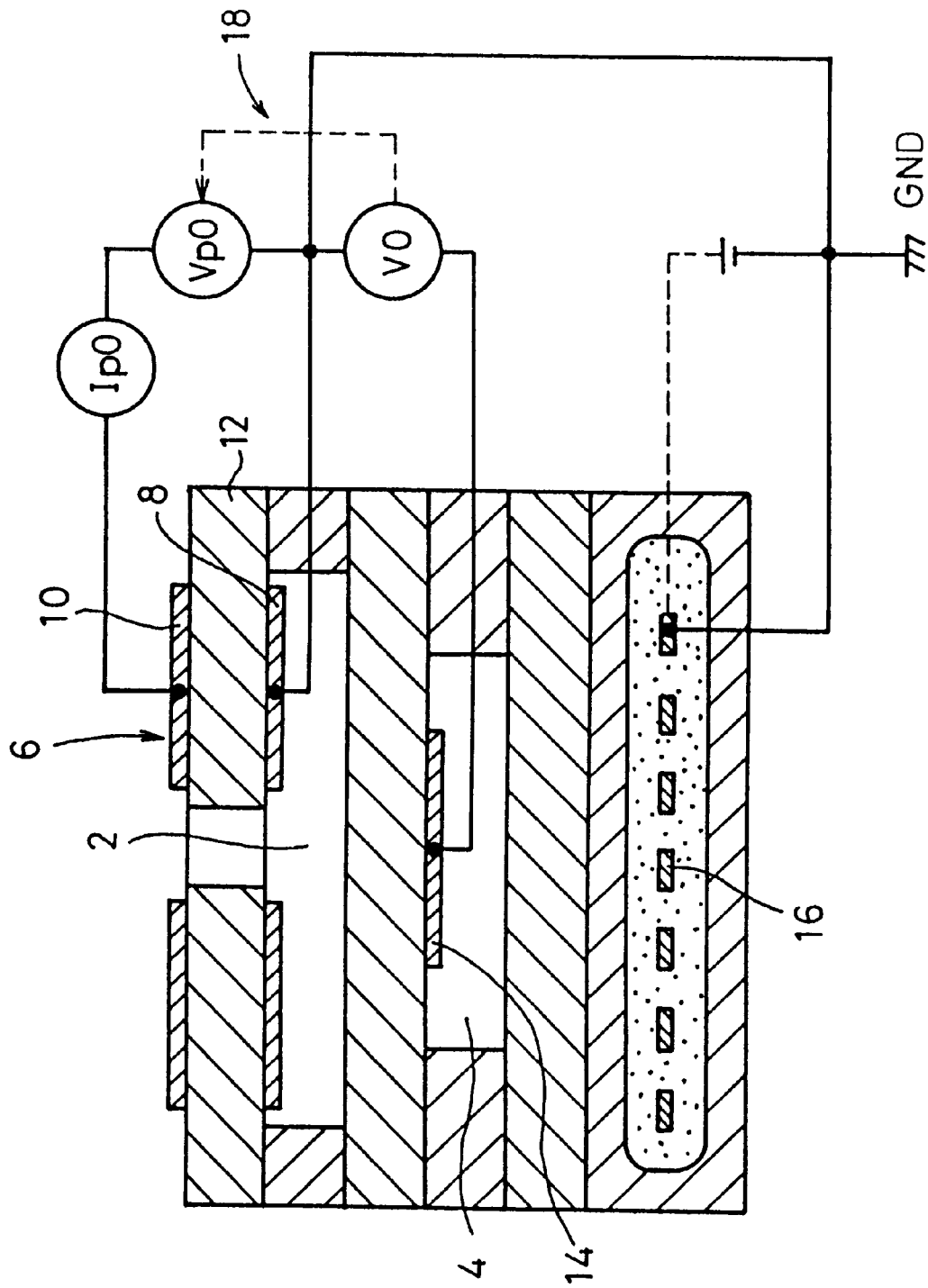
FIG. 7 shows an arrangement of a gas sensor concerning the illustrative conventional technique.

Now, the principle of detection of the gas sensor according to the second embodiment will be explained with reference to a characteristic curve shown in FIG. 6.

At first, when the NO concentration in the external space is 0 ppm, if the oxygen concentration in the atmosphere in the first chamber 58 is controlled by the aid of the feedback control system 74 so that the pumping voltage Vp0 of the main pumping cell 66 has a value ($10^{-7}$ atm) corresponding to 300 mV, then the oxygen concentration in the atmosphere in the second chamber 60 is also $10^{-7}$ atm. Thus, the electromotive force (voltage) V2, which is generated between the detecting electrode 104 and the reference electrode 70 of the oxygen partial pressure-detecting cell 102 provided for the second chamber 60, is about 460 mV.

When the NO concentration in the external space is gradually increased, then the reducing or decomposing reaction of NO is caused on the detecting electrode 104, and the oxygen concentration in the atmosphere around the detecting electrode 104 is increased, because the detecting electrode 104 also functions as an NOx-reducing catalyst in the same manner as the detecting electrode 86 of the measuring pumping cell 90 described above (see FIG. 1). Accordingly, the electromotive force (voltage) V2, which is generated between the detecting electrode 104 and the reference electrode 70, is gradually decreased. With reference to FIG. 6 illustrating the characteristic curve, for example, when the NO concentration increases to 300 ppm, 500 ppm, and 1000 ppm, the electromotive force (voltage) V2 detected by the voltmeter is gradually decreased to 300 mV, 250 mV, and 220 mV respectively.

The degree of the decrease in electromotive force (voltage) V2 represents the NO concentration. In other words, the electromotive force (voltage) V2, which is outputted from the oxygen partial pressure-detecting cell 102 constructed by the detecting electrode 104, the reference electrode 70, and the first solid electrolyte layer 50$d$, represents the NO concentration in the measurement gas.

In the gas sensor according to the second embodiment, the feedback control system 74 for constantly controlling the concentration of oxygen in the measurement gas by means of the pumping operation is also operated as follows, in the same manner as the gas sensor according to the first embodiment. That is, the control operation effected by the feedback control system 74 is not affected by the leak current of the heater, the length of the lead wire, and the heater current (heater output). Thus, it is possible to accurately control the oxygen concentration.

The gas sensors according to the first and second embodiments described above are directed to NOx as the measurement gas component. However, the present invention is also effectively applicable to the measurement for bound oxygen-containing gas components such as $H_2O$ and $CO_2$ other than NOx, in which the measurement is affected by oxygen existing in the measurement gas.

It is a matter of course that the gas sensor according to this invention is not limited to the embodiments described above, which may be constructed in other various forms without deviating from the gist or essential characteristics of this invention.

What is claimed is:

1. A gas sensor comprising:
    a first chamber surrounded by solid electrolytes for introducing measurement gas thereinto and including an external solid electrolyte ontacting an external space;

a main pumping means including said external solid electrolyte contacting with an external space, and an inner pumping electrode and an outer pumping electrode formed on inner and outer surfaces of said external solid electrolyte, for pumping processing a predetermined gas component contained in said measurement gas introduced from said external space on the basis of a control voltage applied between said electrodes to reduce the concentration of said predetermined gas component;

a feedback control system for adjusting said control voltage to give a predetermined level of a voltage between said inner pumping electrode of said main pumping means and a reference electrode disposed at a reference gas introducing portion; and a heater for heating at least said main pumping means to a predetermined temperature, wherein:

said outer pumping electrode of said main pumping means is connected to a ground side lead wire of said heater.

2. The gas sensor according to claim 1, further comprising:

a measuring pumping means including an internal solid electrolyte and a detecting electrode formed on said internal solid electrolyte, for pumping-processing another predetermined gas component contained in said measurement gas after being pumping-processed by said main pumping means, on the basis of a voltage applied between said detecting electrode and said reference electrode; and a current-detecting means for detecting a pumping current generated depending on an amount of said another predetermined gas component pumping-processed by said measuring pumping means.

3. The gas sensor according to claim 2, wherein said measuring pumping means comprises:

said detecting electrode formed at the inside of a second chamber surrounded solid electrolytes for introducing said measurement gas after being pumping-processed by said main pumping means thereinto;

said reference electrode formed in a reference gas introducing chamber surrounded by solid electrolytes for introducing a reference gas thereinto; and said internal solid electrolyte interposed between said detecting electrode and said reference electrode.

4. The gas sensor according to claim 3, further comprising:

a first diffusion rate-determining section provided at a passage to introduce said measurement gas from said external space into said first chamber, for giving a predetermined diffusion resistance to said measurement gas; and a second diffusion rate-determining section provided at a passage to introduce said measurement gas after being pumping-processed by said main pumping means into a second chamber, for giving a predetermined diffusion resistance to said measurement gas.

5. The gas sensor according to claim 4, further comprising a third diffusion rate-determining section provided at a passage for said measurement gas to enter said detecting electrode in said second chamber, for giving a predetermined diffusion resistance to said measurement gas.

6. The gas sensor according to claim 1, further comprising:

a concentration-detecting means including an internal solid electrolyte and a detecting electrode formed on said internal solid electrolyte, for generating an electromotive force corresponding to a difference between an amount of another predetermined gas component contained in said measurement gas after being pumping-processed by said main pumping means and an amount of another said predetermined gas component contained in a reference gas existing on a side of said reference electrode; and a voltage-detecting means for detecting said electromotive force generated by said concentration detecting means.

7. The gas sensor according to claim 6, wherein said concentration-detecting means comprises:

said detecting electrode formed at the inside of a second chamber surrounded by solid electrolytes for introducing said measurement gas after being pumping-processed by said main pumping means thereinto;

said reference electrode formed in a reference gas introducing chamber surrounded by solid electrolytes for introducing a reference gas thereinto; and said internal solid electrolyte interposed between said detecting electrode and said reference electrode.

8. The gas sensor according to claim 7, further comprising:

a first diffusion rate-determining section provided at a passage to introduce said measurement gas from said external space into said first chamber, for giving a predetermined diffusion resistance to said measurement gas; and a second diffusion rate-determining section provided at a passage to introduce said measurement gas after being pumping-processed by said main pumping means into a second chamber, for giving a predetermined diffusion resistance to said measurement gas.

9. The gas sensor according to claim 8, further comprising a third diffusion rate-determining section provided at a passage for said measurement gas to enter said detecting electrode in said second chamber, for giving a predetermined diffusion resistance to said measurement gas.

10. The gas sensor according to claim 1, further comprising an auxiliary feedback control system for adjusting said concentration of said predetermined gas component contained in said measurement gas to be a constant concentration during said pumping process effected by said main pumping means.

11. The gas sensor according to claim 10, wherein said auxiliary feedback control system makes adjustment so that a voltage between an auxiliary pumping electrode formed in the vicinity of a detecting electrode and said reference electrode is at a predetermined level.

* * * * *